United States Patent
Kocur et al.

(10) Patent No.: US 8,114,151 B2
(45) Date of Patent: Feb. 14, 2012

(54) STENT WITH TABS AND HOLES FOR DRUG DELIVERY

(75) Inventors: Gordon J. Kocur, Lino Lakes, MN (US); Daniel Gregorich, St Louis Park, MN (US); Timothy S Girton, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 297 days.

(21) Appl. No.: 12/117,437

(22) Filed: May 8, 2008

(65) Prior Publication Data

US 2009/0281615 A1 Nov. 12, 2009

(51) Int. Cl.
*A61F 2/82* (2006.01)

(52) U.S. Cl. ...................... 623/1.42; 623/1.15

(58) Field of Classification Search .................. 623/1.16, 623/1.15, 1.34, 1.39, 1.46, 1.42, 1.4, 1.1
See application file for complete search history.

(56) References Cited

U.S. PATENT DOCUMENTS

| | | | | |
|---|---|---|---|---|
| 5,843,172 | A * | 12/1998 | Yan | 623/1.42 |
| 6,340,366 | B2 * | 1/2002 | Wijay | 623/1.13 |
| 6,494,889 | B1 * | 12/2002 | Fleischman et al. | 606/155 |
| 6,511,491 | B2 | 1/2003 | Grudem et al. | |
| 6,511,505 | B2 | 1/2003 | Cox et al. | |
| 6,758,859 | B1 * | 7/2004 | Dang et al. | 623/1.15 |
| 6,764,507 | B2 * | 7/2004 | Shanley et al. | 623/1.16 |
| 6,790,230 | B2 * | 9/2004 | Beyersdorf et al. | 623/2.18 |
| 7,060,093 | B2 * | 6/2006 | Dang et al. | 623/1.42 |
| 7,090,694 | B1 * | 8/2006 | Morris et al. | 623/1.15 |
| 7,094,255 | B2 * | 8/2006 | Penn et al. | 623/1.15 |
| 7,135,038 | B1 | 11/2006 | Limon | |
| 7,144,420 | B2 | 12/2006 | Lenz | |
| 7,163,555 | B2 | 1/2007 | Dinn | |
| 7,208,010 | B2 * | 4/2007 | Shanley et al. | 623/1.42 |
| 7,247,166 | B2 * | 7/2007 | Pienknagura | 623/1.15 |
| 7,465,315 | B2 * | 12/2008 | Morris et al. | 623/1.15 |
| 7,527,644 | B2 * | 5/2009 | Mangiardi et al. | 623/1.15 |
| 2002/0143386 | A1 * | 10/2002 | Davila et al. | 623/1.15 |
| 2002/0193871 | A1 * | 12/2002 | Beyersdorf et al. | 623/1.26 |
| 2004/0068316 | A1 | 4/2004 | Schaeffer | |
| 2004/0093066 | A1 * | 5/2004 | Durcan | 623/1.15 |
| 2004/0243217 | A1 | 12/2004 | Andersen et al. | |
| 2005/0070991 | A1 * | 3/2005 | Pienknagura | 623/1.11 |

(Continued)

FOREIGN PATENT DOCUMENTS

WO 2006/020127 A1 2/2006

(Continued)

*Primary Examiner* — Thomas J Sweet
*Assistant Examiner* — Jason-Dennis Stewart
(74) *Attorney, Agent, or Firm* — Vidas, Arrett & Steinkraus

(57) ABSTRACT

A stent can include a tubular body, a plurality of circumferential serpentine bands, a plurality of connectors extending between immediately adjacent serpentine bands, and a plurality of tabs. The plurality of tabs include peak tabs and trough tabs. Each peak tab and each trough tab have a first end and a second end wherein only the first end is engaged to a serpentine band, each peak tab extends substantially parallel to the longitudinal axis from a peak on a serpentine band toward a peak on an immediately distal serpentine band. Each trough tab extends substantially parallel to the longitudinal axis from a trough on a serpentine band toward a trough on an immediately proximal serpentine band. Each serpentine band defines a plurality of holes and each tab defines a plurality of holes. The holes are constructed and arranged to contain a therapeutic agent.

14 Claims, 5 Drawing Sheets

U.S. PATENT DOCUMENTS

| | | |
|---|---|---|
| 2005/0149166 A1* | 7/2005 | Schaeffer et al. ............ 623/1.13 |
| 2005/0149168 A1* | 7/2005 | Gregorich .................... 623/1.15 |
| 2005/0171597 A1* | 8/2005 | Boatman et al. ............. 623/1.22 |
| 2005/0182479 A1* | 8/2005 | Bonsignore et al. ......... 623/1.15 |
| 2006/0224231 A1* | 10/2006 | Gregorich .................... 623/1.16 |
| 2006/0224234 A1* | 10/2006 | Jayaraman ................... 623/1.16 |
| 2007/0123974 A1* | 5/2007 | Park et al. .................... 623/1.16 |
| 2008/0033531 A1* | 2/2008 | Barthel et al. ............... 623/1.15 |
| 2008/0051868 A1* | 2/2008 | Cottone et al. ............... 623/1.11 |
| 2008/0132989 A1* | 6/2008 | Snow et al. ................... 623/1.12 |
| 2008/0147166 A1* | 6/2008 | Bates et al. ................... 623/1.15 |
| 2008/0195189 A1* | 8/2008 | Asgari ........................... 623/1.2 |
| 2008/0234795 A1* | 9/2008 | Snow et al. ................... 623/1.11 |
| 2009/0163991 A1* | 6/2009 | Lenz et al. .................... 623/1.15 |
| 2009/0228088 A1* | 9/2009 | Lowe et al. ................... 623/1.2 |
| 2009/0240317 A1* | 9/2009 | Cottone et al. ............... 623/1.15 |

FOREIGN PATENT DOCUMENTS

WO  2006/099450 A2  9/2006

* cited by examiner

STENT WITH TABS AND HOLES FOR DRUG DELIVERY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents and similar devices such as stent, stent-grafts, expandable frameworks, and similar implantable medical devices, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

One technique which improves the effectiveness of stenotic procedures is to fill reservoirs on the implantable stent with therapeutic agents that are designed to be released in body lumens or vessels. Examples of drug eluting stents are found in U.S. Pat. Nos. 7,135,038 and 7,163,555, the entire contents of each being hereby incorporated by reference.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R §156(a) exists.

All U.S. patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided for the purposes of complying with 37 C.F.R. §172.

BRIEF SUMMARY OF THE INVENTION

In at least one embodiment, the invention is directed to a stent comprising a generally tubular body disposed about a longitudinal axis, the stent having a proximal end and a distal end. The stent comprises a plurality of circumferential serpentine bands having alternating peaks and troughs. Each serpentine band has a wavelength and an amplitude. The peaks of each serpentine band are substantially aligned with the peaks of each immediately adjacent serpentine band. The stent further comprises a plurality of connectors extending between immediately adjacent serpentine bands. The stent further comprises a plurality of tabs comprising peak tabs and trough tabs. Each peak tab and each trough tab have a first end and a second end wherein only the first end is engaged to a serpentine band. Each peak tab extends substantially parallel to the longitudinal axis from a peak on a serpentine band toward a peak on an immediately distal serpentine band. Each trough tab extends substantially parallel to the longitudinal axis from a trough on a serpentine band toward a trough on an immediately proximal serpentine band. Each serpentine band defines a plurality of holes, and each tab defines a plurality of holes Each hole on a serpentine band is located approximately a distance $D_1$ from each immediately adjacent hole on the serpentine band. Each hole on a tab is located approximately distance $D_2$ from each immediately adjacent hole on the tab. The holes are constructed and arranged to contain a therapeutic agent(s).

In some embodiments, distance $D_1$ is substantially equal to distance $D_2$.

In at least one embodiment, distance $D_1$ is greater than distance $D_2$.

In some embodiments, distance $D_1$ is less than distance $D_2$.

In at least one embodiment, each of the plurality of connectors extends from a trough on a serpentine band to a trough on an immediately proximal serpentine band.

In some embodiments, at least one of the plurality of tabs has a connected end and an unconnected end, and a first side and a second side. The first side and the second side extend between the connected end and the unconnected end. The first side and the second side define a width therebetween, the width being substantially constant along the length of the tab.

In at least one embodiment, at least one of the plurality of tabs has a connected end, an unconnected end, and a first side and a second side. The first side and the second side extend between the connected end and the unconnected end. The first side and the second side define a width therebetween, the width being variable along the length of the tab. At least one of the plurality of tabs comprises a first portion having a first width and a second portion having a second width, the second width being greater than the first width.

In some embodiments, at least one hole is positioned in the second portion.

In at least one embodiment, at least one of the plurality of tabs comprises a longitudinal axis, and the at least one hole has a center off of the longitudinal axis.

In some embodiments, each of the plurality of serpentine bands has the same wavelength and amplitude.

In at least one embodiment, each of the plurality of serpentine bands has the same amplitude.

In some embodiments, each of the plurality of serpentine bands has the same wavelength.

In at least one embodiment, each of the plurality of tabs has substantially the same length.

In at least one embodiment, the invention is directed to a stent which comprises a generally tubular body, a plurality of circumferential serpentine bands, a plurality of connectors, and a plurality of tabs. The generally tubular body is disposed about a longitudinal axis and has a proximal end and a distal end. Each serpentine band has alternating peaks and troughs, and each serpentine band comprises a plurality of struts. Each serpentine band has a wavelength and an amplitude. The peaks of each serpentine band are substantially aligned with the troughs of each immediately adjacent serpentine band. The connectors extend between immediately adjacent serpentine bands. The plurality of tabs comprises peak tabs and trough tabs, with each peak tab extending substantially parallel to the longitudinal axis from a peak on a serpentine band toward a trough on an immediately proximal serpentine band, and each trough tab extending substantially parallel to the longitudinal axis from a trough on a serpentine band toward a peak on an immediately distal serpentine band. At least one of the plurality of struts defines at least one hole, and at least one of the plurality of tabs defines at least one hole, the at least one hole constructed and arranged to contain a therapeutic agent.

In some embodiments, at least one of the plurality of connectors includes a hole.

In at least one embodiment, at least one of the plurality of connectors includes a curved region.

In at least one embodiment, the invention is directed to a stent which comprises a generally tubular body, a plurality of circumferential serpentine bands, a plurality of connectors, and at least one circumferential tab column. The generally tubular body is disposed about a longitudinal axis and has a proximal end and a distal end. Each serpentine band has alternating peaks and troughs, and each serpentine band comprises a plurality of struts. Each serpentine band has a wavelength and an amplitude. The peaks of each serpentine band are substantially aligned with the peaks of each immediately adjacent serpentine band. Each peak has a proximal surface and a distal surface and each tough has a proximal surface and distal surface. The distal surface of the peaks of a serpentine band define a peak circumferential plane, the proximal surface of the troughs of a serpentine band define a trough circumferential plane. The connectors extend between immediately adjacent serpentine bands. The at least one tab column is defined by the peak circumferential plane of a serpentine band and the trough circumferential plane of an immediately distal serpentine band. The at least one tab column comprises a plurality of tabs. The plurality of tabs comprises peak tabs and trough tabs, with each peak tab extending substantially parallel to the longitudinal axis from a peak on a serpentine band toward a peak on an immediately distal serpentine band, and each trough tab extending substantially parallel to the longitudinal axis from a trough on a serpentine band toward a trough on an immediately proximal serpentine band. At least one of the plurality of struts defines at least one hole, and at least one of the plurality of tabs defines at least one hole, the at least one hole constructed and arranged to contain a therapeutic agent.

In some embodiments, the proximal surface of the peaks of a serpentine band defines an inner peak circumferential plane, and the distal surface of the troughs of a serpentine band defines an inner trough circumferential plane. The peak tabs extend distally no further than the inner trough circumferential plane. In at least one embodiment, the trough tabs extend proximally no further than the inner peak circumferential plane.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
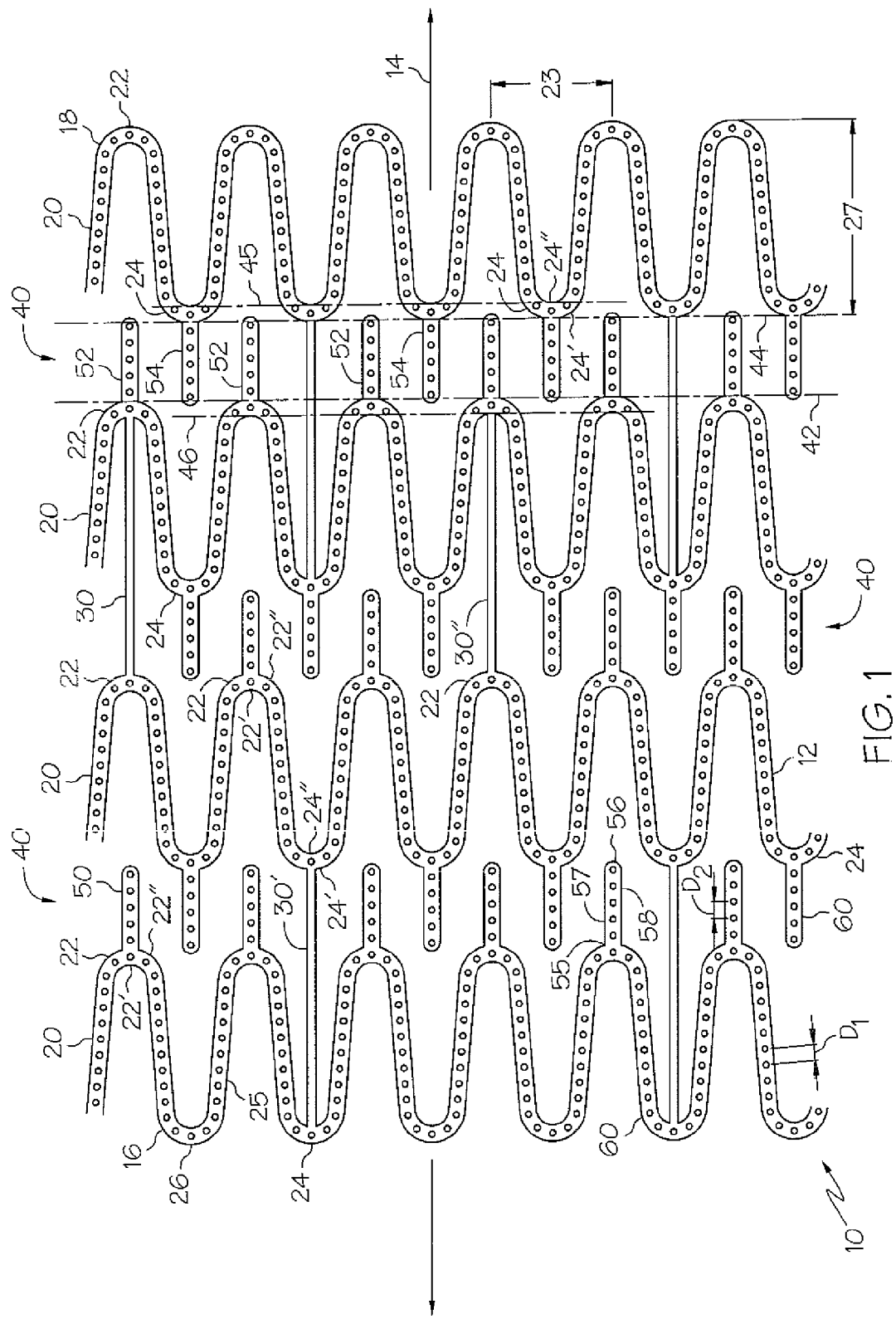
FIG. 1 is a plan view of a portion of a flattened embodiment of the present invention in an unexpanded state.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to FIG. 1, an embodiment of a stent 10 is shown. FIG. 1 depicts stent 10 comprising a generally tubular body 12, a plurality of circumferential serpentine bands 20, a plurality of connectors 30, at least one circumferential tab column 40, a plurality of tabs 50, and a plurality of holes 60.

As shown in FIG. 1, the generally tubular body 12 of the stent is disposed about a longitudinal axis 14. The stent depicted has a proximal end 16 and a distal end 18. Stent 10 includes a plurality of circumferential serpentine bands, shown at 20.

The serpentine bands are longitudinally offset from one another along the longitudinal axis. Each serpentine band 20 includes alternating peaks 22 and troughs 24. It should be noted that the serpentine band 20 may be provided in any suitable arrangement, including patterns (or "waves") characterized by sine and cosine functions as well as patterns which are not rigorously characterized by those functions, but nevertheless resemble such patterns. In a more general way, such patterns include those which are characterized as having one or more peaks and troughs. As an example, a pattern whose peaks and troughs are U shaped or bulbous is intended to be included. Also intended to be included are patterns which are more triangular in shape such as a saw-tooth patterns, or patterns whose peaks and troughs are rectangular. One of ordinary skill will recognize that there are numerous other patterns not mentioned specifically above which may define the serpentine bands.

As seen in FIG. 1, the serpentine bands have a wavelength 23 and an amplitude 27. In the embodiment depicted, the wavelengths 23 of each serpentine band are substantially equal. Also, the amplitudes 27 are substantially equal One of ordinary skill will recognize that it may be desirable for adjacent bands to have different amplitudes, or different wavelengths, so long as the peaks and troughs of adjacent bands align in such a manner as in FIG. 1.

Serpentine bands 20 are comprised of struts 25. The struts 25 may be straight or may be curved, as is shown at 26. Whether straight or curved, the struts will hereinafter be referred to as struts 25. The struts are interconnected in such a way, as is known by those of ordinary skill in the art, to produce the serpentine bands 20.

Still referring to FIG. 1, the connectors 30 extend between immediately adjacent serpentine bands 20. As shown in FIG. 1, immediately adjacent serpentine bands may be connected by connectors 30', which extend between a trough 24 on one serpentine band and a trough 24 on an immediately adjacent serpentine band. And, immediately adjacent serpentine bands maybe connected by connectors 30", which extend between a peak 22 and a peak 22 on an immediately adjacent serpentine band. It should be noted that, while not depicted, the present invention includes embodiments where the connectors 30 extend only between troughs. Similarly, the present invention includes embodiments where the connectors 30 extend only between peaks.

Inventive stent 10 further includes at least one circumferential tab column 40 As depicted in FIG. 1, each peak 22 has a proximal surface 22' and a distal surface 22". Similarly, each trough 24 has a proximal surface 24' and a distal surface 24". The distal surfaces 22" of the peaks of a serpentine band define a peak circumferential plane 42 and the proximal surfaces 24' of the troughs of a serpentine band define a trough circumferential plane 44. Each tab column 40 is defined by the peak circumferential plane 42 of a serpentine band and the trough circumferential plane 44 of an immediately distal serpentine band.

The circumferential tab column 40 comprises a plurality of tabs 50, as shown in FIG. 1. The tabs 50 extend substantially parallel to the longitudinal axis 14 of stent 10. It should be noted that it may be desirable in some embodiments to include tabs which are not straight or do not extend substantially parallel to the longitudinal axis 14. In the embodiment shown in FIG. 1, the tabs 50 of the tab column comprise peak tabs 52 and trough tabs 54.

The peak tabs 52 extend distally from the peak 22 of a serpentine band toward the peak 22 of an immediately distal serpentine band. Peak tabs 52 have an end 55 connected to a serpentine band, and an unconnected end 56. In the embodiment shown in FIG. 1, the peak tabs 52 have a first side 57 and second side 58 which define a substantially constant width along the length of the tab.

The trough tabs 54 extend proximally from the troughs 54 of a serpentine band toward the troughs 54 of an immediately proximal serpentine band. Trough tabs 54 have an end connected to a serpentine band, and an unconnected end. In the embodiment shown in FIG. 1, the trough tabs 54 have first and second sides which define a substantially constant width along the length of the tab. And, in at least some embodiments, the tabs 50 have substantially the same lengths, like in FIG. 1, In some embodiments the tabs 50 are confined substantially within their respective tab columns. In other embodiments the tabs 50 may extend beyond the peak and trough circumferential planes which define their respective tab columns. In some embodiments, a peak tab 52 may extend distally beyond a trough circumferential plane 44, but no further than an inner trough circumferential plane 45 defined by the distal surfaces 24" of the troughs of a serpentine band. Similarly, a trough tab 54 may extend proximally beyond a peak circumferential plane 42. In some embodiments a trough tab 54 may extend proximally beyond an peak circumferential plane 42, but no further than an inner peak circumferential plane 46 defined by the proximal surfaces 22' of the peaks of a serpentine band.

Still referring to FIG. 1, the inventive stent 10 further includes reservoirs or holes 60 that are designed to contain therapeutic agents adapted to be released at the site of the stent's implantation or areas adjacent thereto. The struts 25 and the tabs 50 define the holes 60 such that the holes can contain the therapeutic agent(s). It should be noted that the holes 60 may extend either partially or completely through the thickness of the struts or tabs depending upon the desired design characteristics of the stent.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Referring again to FIG. 1, the holes on the serpentine bands are spaced apart such that each hole on a serpentine band is located approximately a distance $D_1$ from each immediately adjacent hole on the serpentine band. And, the holes on the tabs are spaced apart such that each hole on a tab is located approximately a distance $D_2$ from each immediately adjacent hole on the tab. In some embodiments, distance $D_1$ is substantially equal to distance $D_2$. Providing a uniform distance between the holes on both the tabs and the serpentine bands allows the therapeutic agent to be delivered approximately uniformly at the deployment site. In at least one embodiment, distance $D_1$ is not substantially equal to distance $D_2$, thereby allowing delivery of the therapeutic agent to be varied as necessary at the implantation site For instance, distance $D_1$ may be greater than distance $D_2$, or distance $D_1$ may be less than distance $D_2$.

Figure 2:
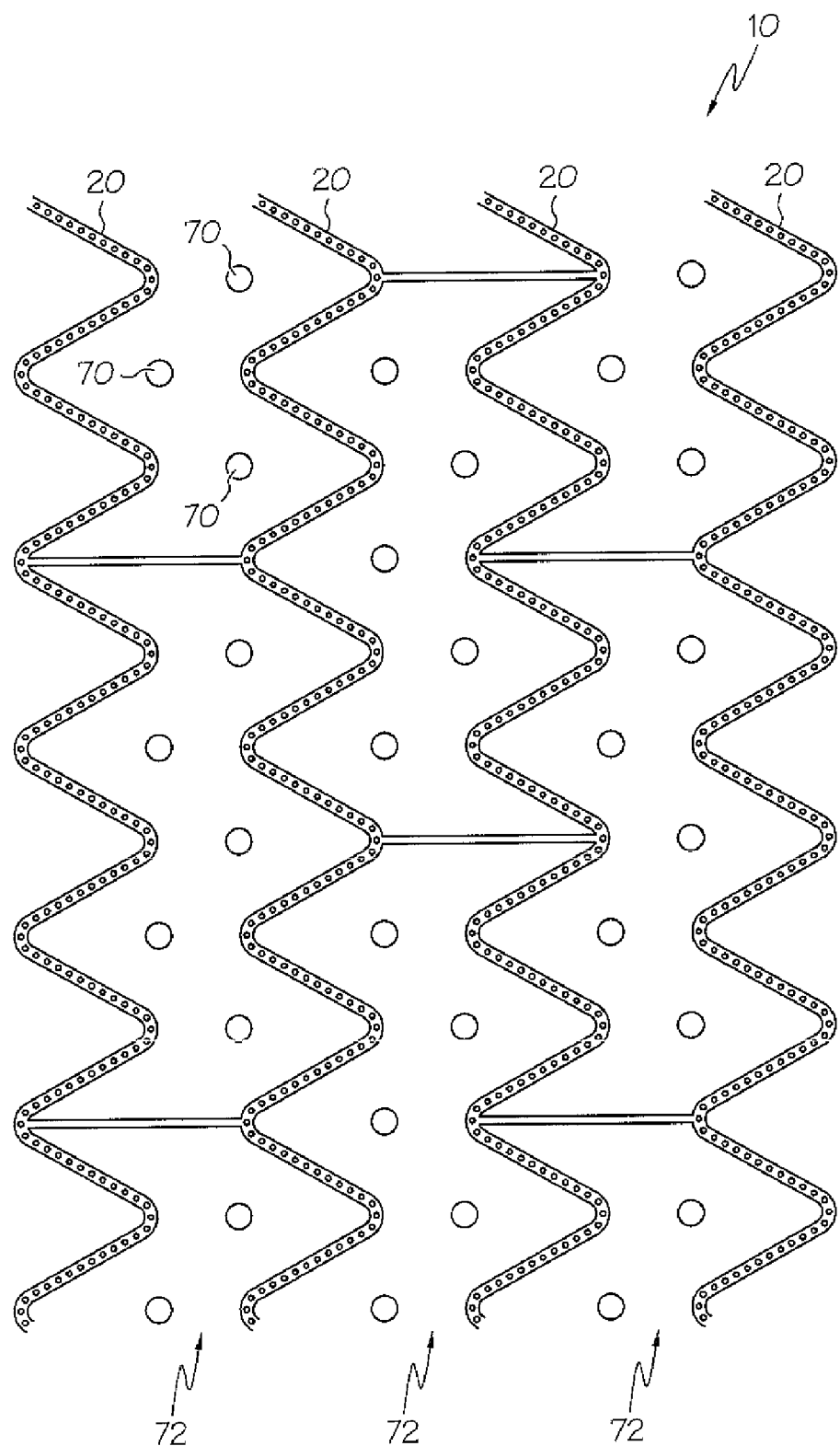
FIG. 2 is a PRIOR ART plan view of a stent without tabs.
Figure 3:
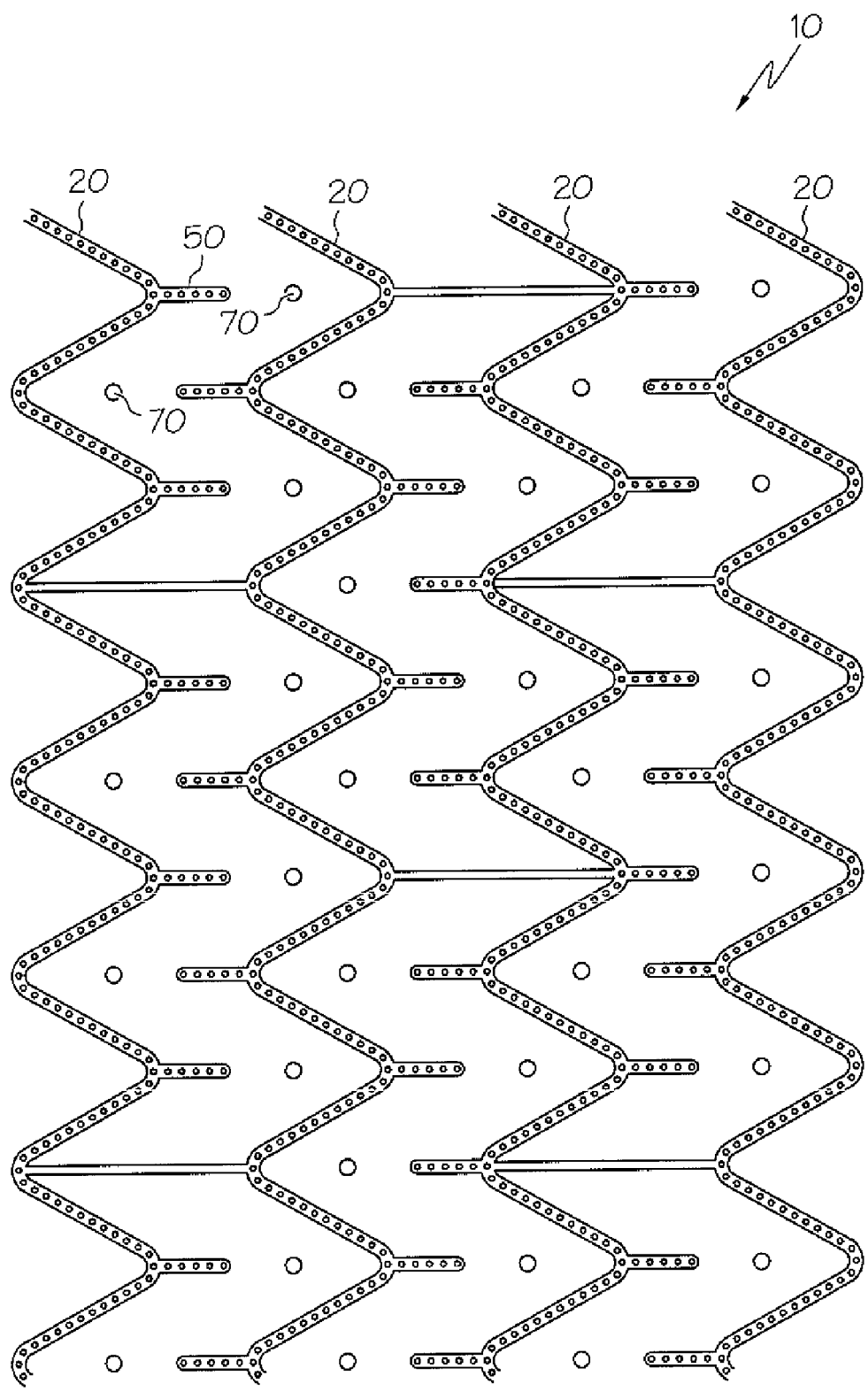
FIG. 3 is a plan view of the embodiment shown in FIG. 1 in an expanded state.

It should be clear that using the tabs as disclosed herein increases the overall surface area of the stent This is shown graphically in FIGS. 2 and 3: FIG. 2 depicts a PRIOR ART stent in an expanded state, without tabs, while FIG. 3 depicts the inventive stent of FIG. 1 in an expanded state. Referring to FIG. 2, reference numbers 70 indicate areas of a body lumen or vessel where it may be desirable to provide stent coverage. In the PRIOR ART stent of FIG. 2, there is no structure of stent 10 which provides coverage to areas 70 of the body lumen or vessel. It is seen in FIG. 2 that the areas 70 of the body lumen or vessel where there is no stent coverage form strips 72 between the serpentine bands 20.

This is in contrast to the inventive stent, shown in FIG. 3 in its expanded state. The tabs 50 extend such that the strips 72 without stent coverage depicted in FIG. 2 are eliminated. That is, the stent 10 with tabs 50 reduces the areas of the body lumen or vessel where there is no stent coverage. Therefore, the uniformity of stent coverage is improved.

By providing extra surface area to the inventive stent via the tabs, and by filling the holes on the tabs with therapeutic agents, the inventive stent also improves overall drug release coverage. Overall drug release is more uniform using the inventive stent because the open regions of the body lumen or vessel are reduced.

Figure 4:
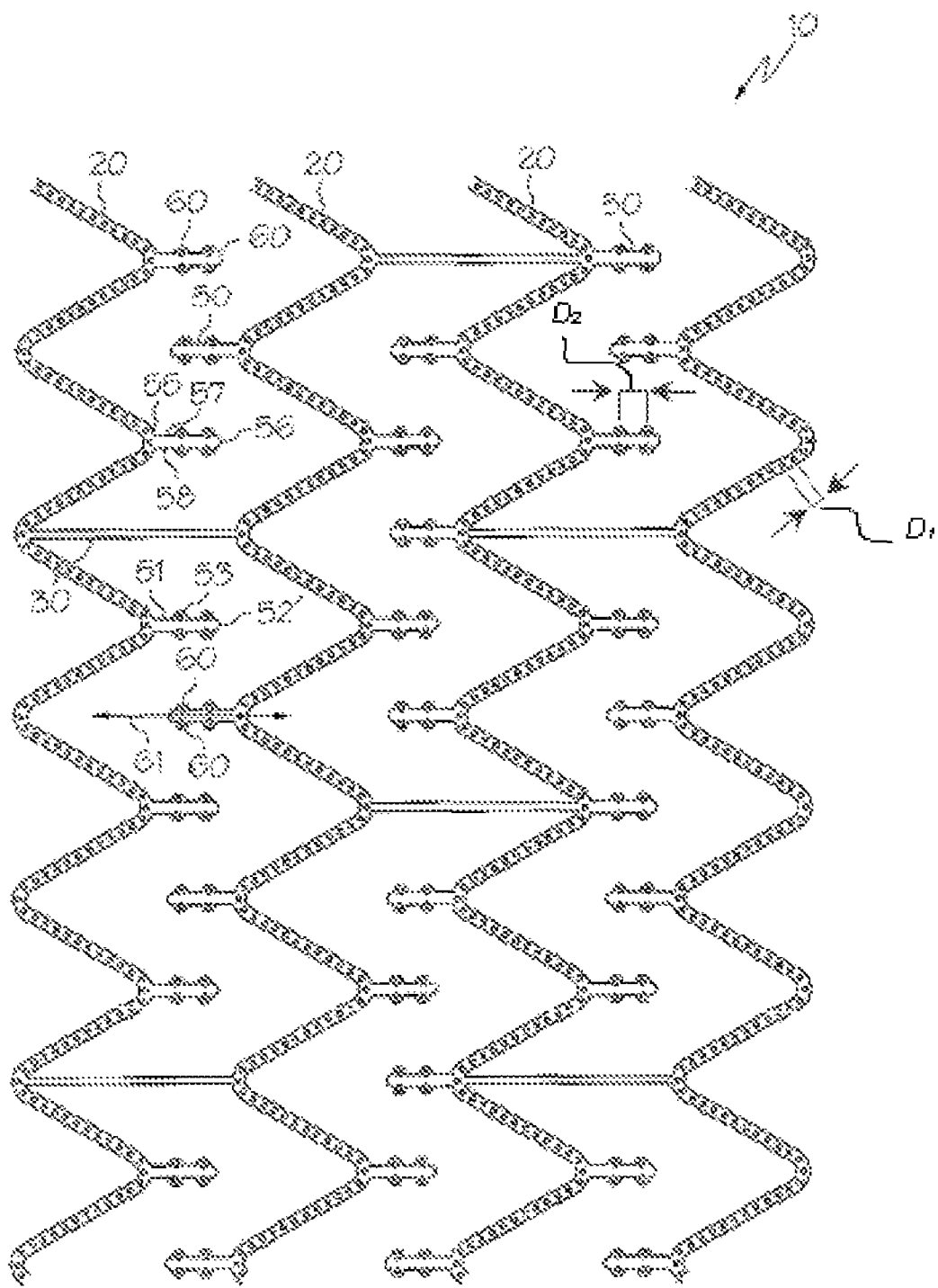
FIG. 4 is a plan view of an alternative embodiment of the present invention.
Figure 5:
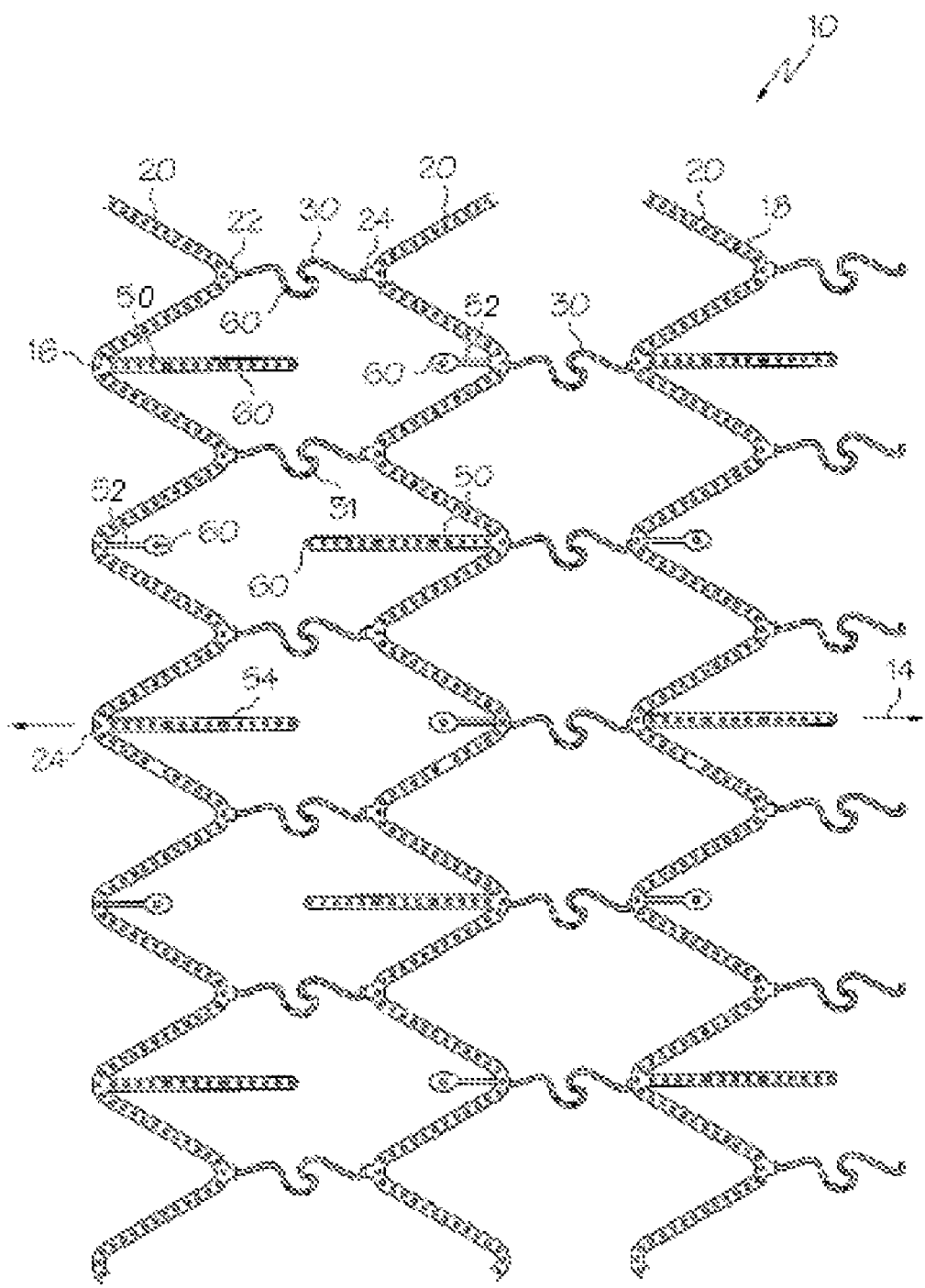
FIG. 5 is a plan view of an alternative embodiment of the present invention.

Other embodiments of the inventive stent 10 are shown in FIGS. 4 and 5. Referring now to FIG. 4, the tabs 50 have a first side 57 and second side 58 which define a width, like in FIG. 1. In the embodiment in FIG. 4, however, the width is variable along the length of the tab. Peak tab 52', for example, has a first portion 51 having a first width and a second portion 53 having a second width, and as seen in FIG. 4, the second width is greater than the first width. The tabs 50, depicted in FIG. 4 with a longitudinal axis 61, have holes 60 centered off of the tab's longitudinal axis 61. In addition, the holes 60 are positioned within the second, or wider, portion 53 of the tab. By constructing the tabs as in FIG. 4, the amount of surface area of the stent may be increased beyond that which is produced with the embodiment shown in FIG. 1, thereby allowing additionally drug coverage, if desired.

Referring now to FIG. 5, another embodiment of the inventive stent is depicted. In contrast to the embodiment in FIG. 1, the serpentine bands 20 are approximately 180 degrees out of phase. That is, a first serpentine band is approximately 180 degrees out of phase with an immediately adjacent second band because each trough of the band is substantially longitudinally aligned with an opposing peak of an immediately adjacent band. The bands in FIG. 1 are in phase because their respective peaks and troughs are substantially longitudinally aligned. Furthermore, the embodiment depicted in FIG. 5 shows that connectors 30 may include a curved region 31, rather than being straight and substantially parallel to the longitudinal axis of the stent, like in FIG. 1. It may be desirable to include holes 60 in the connector 30 to further increase drug coverage, as shown in FIG. 5.

Another important feature of the embodiment depicted in FIG. 5 is that the tabs on one band are substantially longitudinally aligned with and extend towards the tabs on an immediately adjacent band. That is, the tabs in FIG. 5 are not circumferentially aligned in a tab column, like in FIG. 1. Rather, trough tabs 54 extend distally from troughs 24 towards the immediately adjacent band, and in particular towards peak tab 52. Peak tab 52, on the other hand, extends proximally from a band towards the immediately adjacent band, and in particular towards trough tab 54.

Another feature of the embodiment in FIG. 5 is that the tabs 50 are not of equal lengths. With such an embodiment, it is seen that areas 70 presented in FIG. 3 may be further reduced.

It should be noted that it in some embodiments it may be desirable to construct stent 10 such that the peak and trough tabs are not substantially longitudinally aligned, but instead are offset longitudinally.

In some embodiments, it may be desirable to include another mechanism for the delivery of a therapeutic agent. Often the agent will be in the form of a coating or other layer (or layers) of material placed on a surface region of the stent, which is adapted to be released at the site of the stent's implantation or areas adjacent thereto.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent comprising:
   a generally tubular body disposed about a longitudinal axis, the stent having a proximal end and a distal end;
   a plurality of circumferential serpentine bands, each serpentine band having alternating peaks and troughs, each serpentine band having a wavelength and an amplitude, the peaks of each serpentine band being substantially aligned with the peaks of each immediately adjacent serpentine band;
   a plurality of connectors, the connectors extending between immediately adjacent serpentine bands; and
   a plurality of tabs, the plurality of tabs comprising peak tabs and trough tabs, each peak tab and each trough tab having a first end and a second end wherein only the first end is engaged to a serpentine band, each peak tab extending substantially parallel to the longitudinal axis from a peak on a serpentine band toward a peak on an immediately distal serpentine band, each trough tab extending substantially parallel to the longitudinal axis from a trough on a serpentine band toward a trough on an immediately proximal serpentine band,
   wherein each serpentine band defines a plurality of holes, each hole on a serpentine band being located approximately a distance $D_1$ from each immediately adjacent hole on the serpentine band, and
   wherein each tab defines a plurality of holes, each hole on a tab being located approximately a distance $D_2$ from each immediately adjacent hole on the tab, the holes constructed and arranged to contain a therapeutic agent.

2. The stent of claim 1, wherein each of the plurality of connectors extends from a trough on a serpentine band to a trough on an immediately proximal serpentine band.

3. The stent of claim 1, wherein at least one of the plurality of tabs has a connected end and an unconnected end, and a first side and a second side, the first side and the second side extending between the connected end and the unconnected end, the first side and the second side defining a width therebetween, the width being substantially constant along the length of the tab.

4. The stent of claim 1, wherein at least one of the plurality of tabs has a connected end, an unconnected end, and a first side and a second side, the first side and the second side extending between the connected end and the unconnected end, the first side and the second side defining a width therebetween, the width being variable along the length of the tab, the at least one of the plurality of tabs comprising a first portion having a first width and a second portion having a second width, the second width being greater than the first width.

5. The stent of claim 4, wherein the at least one hole is positioned in the second portion.

6. The stent of claim 5, wherein the at least one of the plurality of tabs comprises a longitudinal axis, the at least one hole having a center off of the longitudinal axis.

7. The stent of claim 1, wherein each of the plurality of serpentine bands has the same wavelength and amplitude.

8. The stent of claim 1, wherein each of the plurality of serpentine bands has the same amplitude.

9. The stent of claim 1, wherein each of the plurality of serpentine bands has the same wavelength.

10. The stent of claim 1, wherein each of the plurality of tabs has substantially the same length.

11. The stent of claim 1, wherein $D_1$ is substantially equal to $D_2$.

12. The stent of claim 1, wherein $D_1$ is greater than $D_2$.

13. The stent of claim 1, wherein $D_1$ is less than $D_2$.

14. A stent comprising:
a generally tubular body disposed about a longitudinal axis, the stent having a proximal end and a distal end;
a plurality of circumferential serpentine bands, each serpentine band having alternating peaks and troughs, each serpentine band having a wavelength and an amplitude, the peaks of each serpentine band being substantially aligned with the peaks of each immediately adjacent serpentine band;
a plurality of connectors, the connectors extending between immediately adjacent serpentine bands, wherein each of the plurality of connectors extends from a trough on a serpentine band to a trough on an immediately proximal serpentine band; and
a plurality of tabs, the plurality of tabs comprising peak tabs and trough tabs, each peak tab and each trough tab having a first end and a second end wherein only the first end is engaged to a serpentine band, each peak tab extending substantially parallel to the longitudinal axis from a peak on a serpentine band toward a peak on an immediately distal serpentine band, each trough tab extending substantially parallel to the longitudinal axis from a trough on a serpentine band toward a trough on an immediately proximal serpentine band,
wherein each serpentine band defines a plurality of holes, each hole on a serpentine band being located approximately a distance $D_1$ from each immediately adjacent hole on the serpentine band, and
wherein each tab defines a plurality of holes each hole on a tab being located approximately a distance $D_2$ from each immediately adjacent hole on the tab, the holes constructed and arranged to contain a therapeutic agent.

* * * * *